(12) United States Patent
Kim

(10) Patent No.: US 9,283,062 B2
(45) Date of Patent: *Mar. 15, 2016

(54) DEVICE AND SYSTEM FOR DENTAL APPLICATIONS AND METHOD RELATING THERETO

(71) Applicant: Dental Lab Aesthetics, LLC, Port Washington, NY (US)

(72) Inventor: Jason J. Kim, Manhasset, NY (US)

(73) Assignee: Dental Lab Aesthetics, LLC, Port Washington, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/200,389

(22) Filed: Mar. 7, 2014

(65) Prior Publication Data

US 2014/0255867 A1    Sep. 11, 2014

Related U.S. Application Data

(63) Continuation-in-part of application No. 13/788,723, filed on Mar. 7, 2013, now Pat. No. 8,672,677.

(51) Int. Cl.
*A61C 9/00* (2006.01)
*A61C 19/10* (2006.01)
*A61C 19/06* (2006.01)

(52) U.S. Cl.
CPC .............. *A61C 19/10* (2013.01); *A61C 9/0006* (2013.01); *A61C 19/066* (2013.01)

(58) Field of Classification Search
CPC ..... A61C 9/0006; A61C 19/10; A61C 19/066

USPC ..................... 433/26, 37, 41, 43, 45
See application file for complete search history.

(56) References Cited

U.S. PATENT DOCUMENTS

| | | |
|---|---|---|
| 305,900 A | 9/1884 | Crowther |
| 880,328 A | 2/1908 | Sadler |
| 1,464,987 A | 8/1923 | Haggard et al. |
| 1,486,039 A * | 3/1924 | Santos ............. 433/43 |
| 1,493,417 A | 5/1924 | Arnett |
| 1,608,632 A | 11/1926 | Strusser |
| 1,634,717 A | 7/1927 | Light |
| 2,549,184 A | 4/1951 | Eliot |
| 3,405,446 A | 10/1968 | Wiener |
| 4,227,877 A | 10/1980 | Tureaud |
| 4,375,965 A | 3/1983 | Weissman |
| 4,484,890 A | 11/1984 | Jouvin |

(Continued)

FOREIGN PATENT DOCUMENTS

DE    19919376 A1 * 11/2000 ............... A61C 5/00
JP    2003-260073 A    9/2003

OTHER PUBLICATIONS

Translation of DE 19919376 reterived on May 13, 2015.*

(Continued)

*Primary Examiner* — Heidi M Eide
(74) *Attorney, Agent, or Firm* — Greenberg Traurig, LLP

(57) ABSTRACT

The present invention relates to various devices, systems, kits and methods having dental applications. For instance, a dental tray is provided for use in taking an impression of a person's teeth. A dental shade chart is also provided and includes a shade sticker for use in determining the shade of a person's tooth. Further, the dental tray and/or the shade chart can be included in a kit.

10 Claims, 9 Drawing Sheets

(56) References Cited

U.S. PATENT DOCUMENTS

| | | |
|---|---|---|
| 4,530,662 A | 7/1985 | Andersson |
| 4,689,010 A | 8/1987 | Wolfe |
| 4,907,966 A | 3/1990 | Kesling |
| 5,316,474 A | 5/1994 | Robertson |
| 5,336,086 A | 8/1994 | Simmen |
| 5,513,985 A | 5/1996 | Robertson |
| 5,772,432 A | 6/1998 | Jordan |
| 5,916,653 A * | 6/1999 | Kunstadter et al. ......... 428/42.1 |
| 6,079,977 A | 6/2000 | Persichetti |
| 6,213,768 B1 | 4/2001 | Wright |
| 6,302,690 B1 | 10/2001 | Brandhorst et al. |
| 6,315,554 B1 * | 11/2001 | Coste et al. ................... 433/26 |
| 6,428,315 B1 | 8/2002 | Prestipino |
| 6,457,973 B1 | 10/2002 | Fetz et al. |
| 6,629,841 B1 | 10/2003 | Skinner |
| 6,749,428 B2 | 6/2004 | DiMarino et al. |
| 6,875,016 B2 | 4/2005 | Burgio et al. |
| 7,021,929 B2 | 4/2006 | DiMarino et al. |
| 7,125,251 B2 | 10/2006 | Livolsi |
| 7,273,371 B2 | 9/2007 | Massad |
| 8,672,677 B1 | 3/2014 | Kim |
| 2004/0224278 A1 * | 11/2004 | Zun ............................... 433/26 |
| 2005/0202362 A1 * | 9/2005 | Ostler et al. .................. 433/26 |
| 2007/0148612 A1 | 6/2007 | Massad |
| 2008/0096158 A1 | 4/2008 | Dorfman |
| 2008/0308450 A1 * | 12/2008 | Tchouangang ............... 206/570 |
| 2008/0311536 A1 | 12/2008 | Kim et al. |
| 2009/0215003 A1 | 8/2009 | Swain et al. |
| 2010/0304323 A1 * | 12/2010 | Rohner et al. .................. 433/26 |
| 2012/0064477 A1 | 3/2012 | Schmitt |
| 2013/0052613 A1 | 2/2013 | Chetiar et al. |

OTHER PUBLICATIONS

"Directed Flow Impression Tray", http://solutions.3m.com.au/wps/portal/3M/en_AU/3M-ESPE-APAC/dental-professionals/products/category/impression/directed-flow-impression-tray/ (copyright notice date 2013) (1 page).

"Traxodent Hemodent Paste Retraction System", http://www.premusa.com/dental/prosthetic.asp (copyright notice date 2000-2004) (7 pages).

"NeoTray Quadrant Impression Trays", http://practicon.com/product.aspx?id=39500 (copyright notice date 2013) (2 pages).

"Partial Mouldable Border-Lock Disposable Impression Tray", http://www.borderlock.com/disposable.htm (copyright notice date 2012) (5 pages).

International Search Report and Written Opinion dated Jul. 1, 2014, issued by the Korean Intellectual Property Office in Applicant's related International (PCT) Application No. PCT/US2014/021605 (18 pages).

* cited by examiner

US 9,283,062 B2

DEVICE AND SYSTEM FOR DENTAL APPLICATIONS AND METHOD RELATING THERETO

CROSS-REFERENCE TO RELATED APPLICATION

This application is a continuation-in-part of U.S. application Ser. No. 13/788,723 filed Mar. 7, 2013, the disclosure of which is incorporated herein by reference in its entirety.

FIELD OF THE INVENTION

The present invention relates to devices and systems for dental applications and methods relating thereto.

BACKGROUND OF THE INVENTION

Various devices useful in the dental field have been developed in the past. For instance, U.S. Pat. Nos. 305,900, 880, 328, 1,464,987, 1,486,039, 1,493,417, 1,608,632, 1,634,717, 2,549,184, 4,227,877, 4,375,965, 4,484,890, 4,530,662, 4,689,010, 4,907,966, 5,336,086, 5,772,432, 6,079,977, 6,213,768 6,302,690, 6,428,315, 6,457,973, 6,629,841, 6,749,428, 7,125,251 and 7,273,371 and U.S. Patent Publication No. 2008/0311536 each disclose a device for taking an impression of a patient's teeth. In one aspect, the present invention relates to a dental tray useful in taking an accurate dental impression.

Various devices have also been developed for determining the shade of a person's teeth (see, e.g., U.S. Pat. Nos. 4,207,678, 4,810,193, 4,919,617, 4,978,296, 5,261,815, 5,588,834, 5,685,712, 5,692,900, 5,725,372, 6,354,835 and 6,755,646). In another aspect, the present invention relates to a shade chart to aid a user in determining his/her teeth shade. The present invention contemplates various additional features and aspects, which are discussed below.

SUMMARY OF THE INVENTION

In accordance with an embodiment of the present invention, a dental tray for use in taking an impression of a person's teeth is provided. More particularly, the dental tray includes a first section having a longitudinal axis and a second section sized and shaped so as to be mounted at least partially within the first section. The first and second sections are sized and shaped so as to define a trough therebetween for receiving an impression-taking material. The second section is adapted to move relative to the first section in a first direction substantially parallel to the longitudinal axis of the first section. The second section has at least one member movable in a second direction substantially perpendicular to the longitudinal axis in response to the movement of the second section in the first direction.

In accordance with another embodiment of the present invention, a dental tray for use in taking an impression of a person's teeth includes a first section having a longitudinal axis and a generally U-shaped outer wall and a second section having a dome-shaped inner member sized and shaped so as to be mounted at least partially within the U-shaped wall of the first section. The U-shaped wall and the dome-shaped member are sized and shaped so as to define a trough therebetween for receiving an impression-taking material. The second section is movable relative to the first section in a first direction which is substantially parallel to the longitudinal axis of the first section. The dome-shaped member has first and second movable members movably attached to the second section. Each of the first and second movable members is movable in a second direction substantially perpendicular to the longitudinal axis in response to the movement of the second section in the first direction.

Another embodiment of the present invention involves providing a dental tray for use in taking an impression of a person's teeth. More particularly, the tray includes a first section having a longitudinal axis and first and second ends spaced apart from one another in a first direction substantially parallel to the longitudinal axis of the first section. The tray also includes second section sized and shaped so as to be mounted at least partially within the first section. The first and second sections are sized and shaped so as to define a trough therebetween for receiving an impression-taking material therein. The second section is adapted for movement relative to the first section in the first direction and has first and second movable members, each of which is movable in a second direction substantially perpendicular to the longitudinal axis in response to the movement of the second section in the first direction.

A further embodiment of the present invention provides a dental tray for use in taking an impression of a person's teeth. The dental tray includes a first section having a longitudinal axis and a generally U-shaped outer wall and including first and second ends spaced apart from one another in a first direction substantially parallel to the longitudinal axis of the first section. The dental tray also includes a second section having a dome-shaped inner member sized and shaped so as to be mounted at least partially within the U-shaped wall of the first section. The U-shaped wall and the dome-shaped member are sized and shaped so as to define a trough therebetween for receiving an impression-taking material therein. The second section is movable relative to the first section in the first direction. The dome-shaped member has first and second movable members, each of which is movable in a second direction substantially perpendicular to the longitudinal axis in response to the movement of the second section in the first direction.

In accordance with yet another embodiment of the present invention, a method for taking an impression of a person's teeth with the use of a dental tray is provided. More particularly, the dental tray includes a first section and a second section. The second section is mounted at least partially within the first section so as to define a trough therebetween and is movable relative to the first section in a first direction which is substantially parallel to a longitudinal axis of the first section. The second section has at least one member movable in a second direction substantially perpendicular to the longitudinal axis in response to the movement of the second section in the first direction. The method includes the steps of placing an impression-taking material in the trough of the tray and inserting the tray into a mouth of the person. The method also includes the steps of moving the tray such that the teeth are inserted into the impression material placed in the trough and moving the second section in the first direction so as to cause the at least one member to move in the second direction.

A further embodiment of the present invention provides a method for taking an impression of a person's teeth with the use of a dental tray having a first section and a second section. The first section has a longitudinal axis and a generally U-shaped outer wall, while the second section has a dome-shaped inner member mounted at least partially within the U-shaped wall of the first section so as to define a trough therebetween. The second section is movable relative to the first section in a first direction substantially parallel to the longitudinal axis of the first section. The dome-shaped member has first and second movable members, each of which is movable in a second direction substantially perpendicular to the longitudinal axis in response to the movement of the second section in the first direction. The method includes the steps of: placing an impression-taking material in the trough of the tray; inserting the tray into a mouth of the person; moving the tray such that the teeth are inserted into the impression material placed in the trough; and moving the second section in the first direction so as to cause the first and second movable members to move in the second direction.

Yet another embodiment involves providing a device for use in determining the shade of a person's tooth, which has a front surface. More particularly, the device includes at least one sticker having a predetermined shade. The at least one sticker has a size smaller than the tooth and configured so as to be removably attached to the front surface of the tooth such that the at least one sticker can be superimposed directly on the front surface of the tooth.

In accordance with a further embodiment, a kit includes a device for use in determining the shade of a person's tooth having a front surface. The device is provided with at least one sticker having a predetermined shade. The at least one sticker has a size smaller than the tooth and configured so as to be removably attached to the front surface of the tooth such that the at least one sticker can be superimposed directly on the front surface of the tooth. The kit may also include a dental tray for taking an impression of a person's teeth or a dental whitening kit having at least one of a whitening gel or strip.

Another embodiment relates to a method for determining the shade of a person's tooth using a sticker having a size smaller than a size of the tooth and having a predetermined shade and a surface. The method includes the steps of removably attaching the sticker to a front surface of the tooth such that the sticker is superimposed directly on the front surface of the tooth; and comparing the shade of the tooth to the shade of the sticker so as to determine the shade of the tooth. The method further includes the step of applying a liquid substance having an adhesive property to at least one of the surface of the sticker and the front surface of the sticker prior to the performance of the attaching step so as to removably attach the sticker the front surface of the tooth. In accordance with one embodiment, the liquid substance includes the person's saliva. In accordance with a further embodiment, the applying step includes the step of licking at least one of the surface of the sticker and the front surface of the tooth such that the sticker is removably attached to the front surface of the tooth by the adhesive property of the saliva. According to yet another embodiment, the comparing step includes the steps of taking a photograph of the tooth with the sticker attached thereto, transmitting the photograph to a processor, and comparing the shade of the tooth to the shade of the sticker, the shade of the sticker being used as a reference shade.

BRIEF DESCRIPTION OF THE DRAWINGS

For a more complete understanding of the present invention, reference is made to the following detailed description of exemplary embodiments considered in conjunction with the accompanying drawings, in which.

DETAILED DESCRIPTION OF THE INVENTION

In accordance with embodiments of the present invention, various devices, systems, kits and/or methods are provided for use in dental applications. These devices, systems, kits and methods are discussed below.

Figure 1:
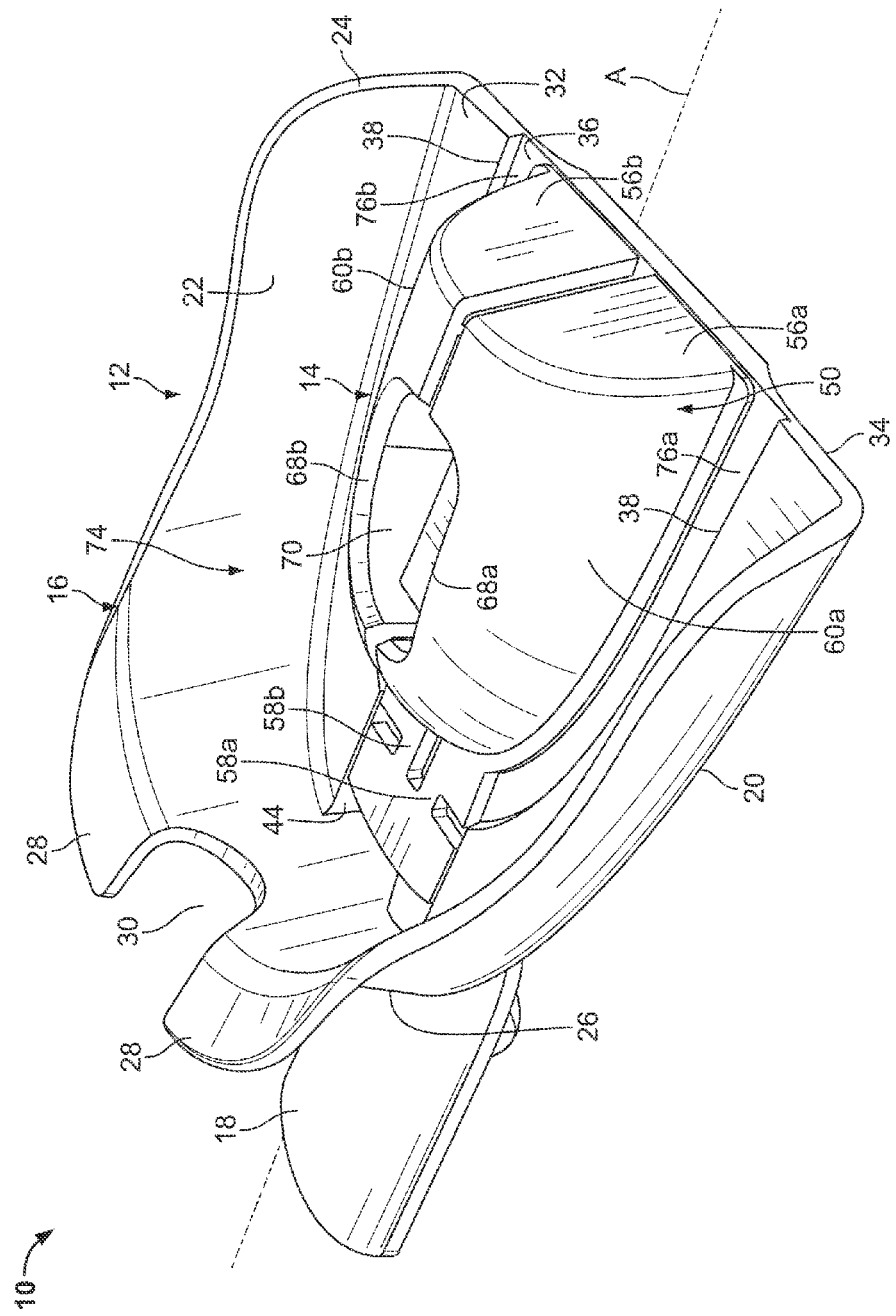
FIG. 1 is a top perspective view of a dental tray constructed in accordance with an embodiment of the present invention.
Figure 2:
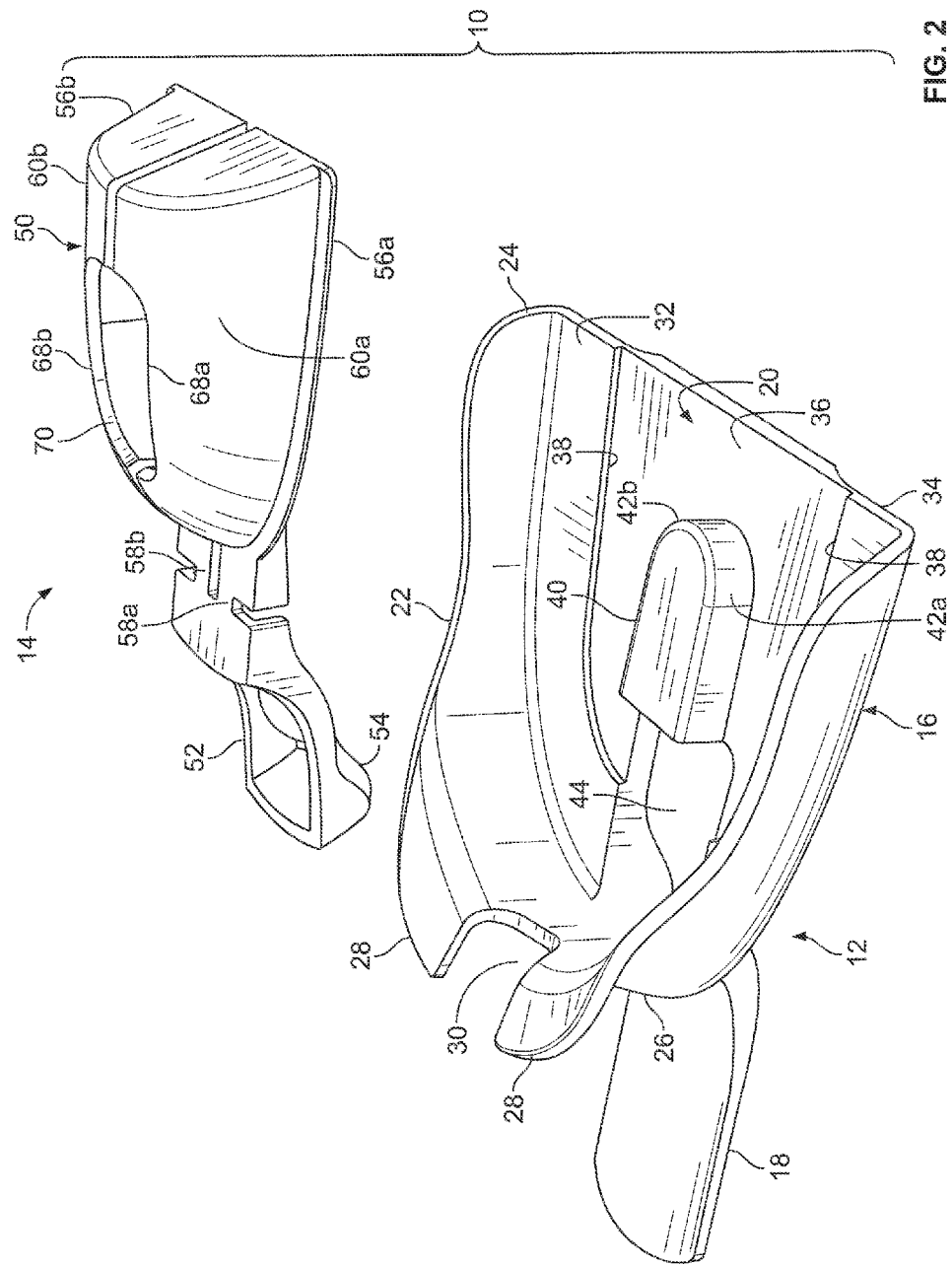
FIG. 2 is an exploded, upper perspective view of the dental tray shown in FIG. 1.

With reference to FIGS. 1 and 2, there is shown a dental tray assembly 10 constructed in accordance with an embodiment of the present invention. More particularly, the dental tray assembly 10, which is adapted for use in taking an impression of upper teeth of a person or a patient, has a longitudinal axis A and includes an outer tray member (i.e., section) 12 and an inner tray member (i.e., section) 14 movably mounted on the outer member 12. The construction of the inner and outer members 12, 14 will be discussed in greater detail below.

Still referring to FIGS. 1 and 2, the outer member 12 includes a tray 16 and a handle 18 extending from the tray 16. More particularly, the tray 16 is provided with a base plate 20, which extends generally in a horizontal manner, and a generally U-shaped outer wall 22, which projects generally vertically from the base plate 20. The tray 16 has an open rear end 24 and a front end 26, which is enclosed by the outer wall 22. Lip support members 28 extend from the outer wall 22 at the front end 26 of the tray 16 for supporting a patient's upper lip when the tray assembly 10 is inserted into the patient's mouth. A notch 30 is provided between the lip support members 28 and extends partially into the outer wall 22 at the front end 26.

Figure 3:
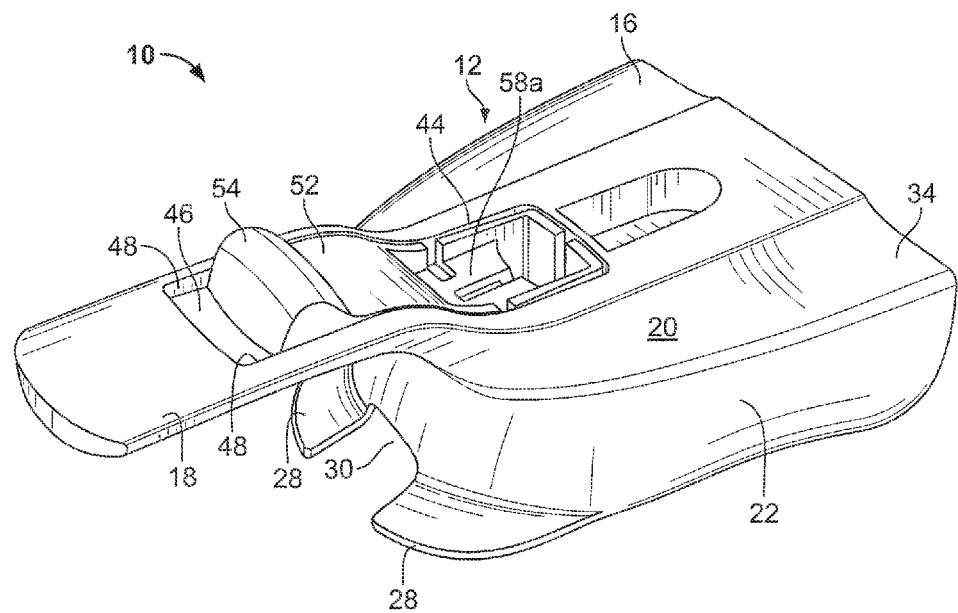
FIG. 3 is a bottom perspective view of the dental tray shown in FIG. 1.

Now referring to FIGS. 1, 2 and 3, the base plate 20 of the tray 16 includes an upper side 32 and a lower side 34. A recessed area 36 is provided generally centrally in the base plate 20. The recessed area 36 has a slightly lower elevation compared to the rest of the upper side 32 of the base plate 20 such that an edge 38 is formed on the upper side 32 defining the recessed area 36. A ramp 40 projects upwardly from the base plate 20 and has a pair of generally curved guide wall portions 42a, 42b on opposite sides thereof. An opening 44 is formed in the base plate 20 adjacent the front end 26 of the tray 16 for purposes to be discussed below. A track 46 is provided in the handle 18 and is defined by a pair of axially extending support walls 48 (see FIG. 3).

Figure 4:
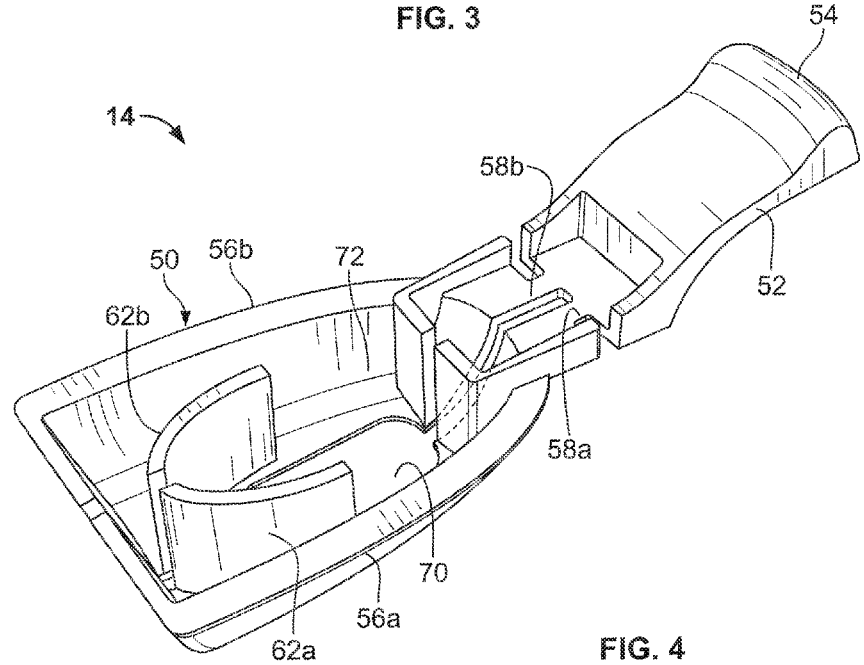
FIG. 4 is a bottom perspective view of an inner member of the dental tray shown in FIG. 1.

With reference to FIGS. 1, 2 and 4, the inner member 14 includes a compression section 50 and a handle 52 extending from the compression section 50 and having a tab 54 at an end thereof. More particularly, the compression section 50 is generally dome-shaped and includes a plurality of compression members 56a, 56b connected to the handle 52 via hinges 58a, 58b (e.g., living hinges), respectively, such that they are laterally pivotable toward or away from each other. More particularly, the compression member 56a is an element that is separate and independent from the compression member 56b. The compression members 56a, 56b have curved, half-dome-shaped walls 60a, 60b, respectively, and curved guides 62a, 62b, respectively. The guides 62a, 62b depend from the walls 60a, 60b, respectively, and are sized and shaped so as to engage the curved wall portions 42a, 42b, respectively, of the outer member 12 (see FIG. 6) for purposes to be discussed hereinbelow.

Figure 5:
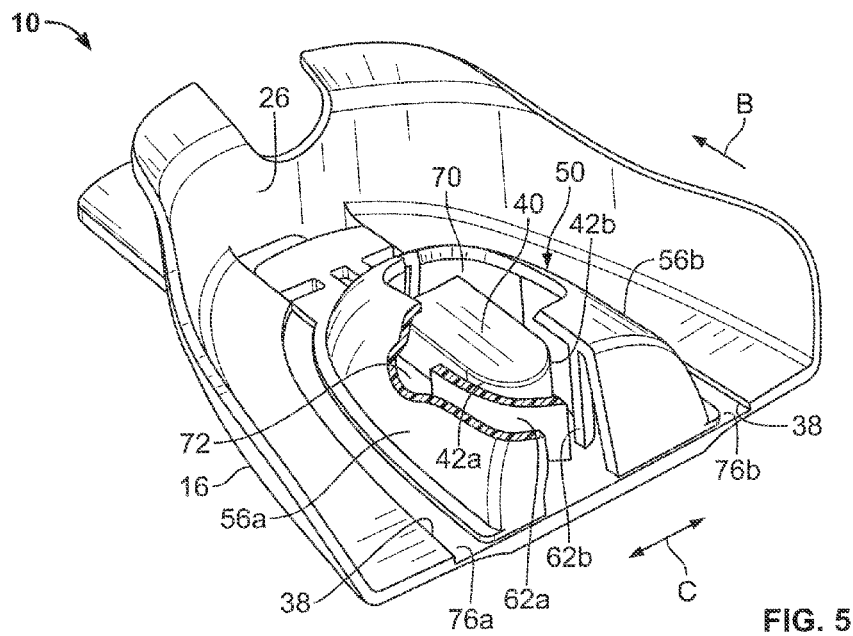
FIGS. 5 and 6 are perspective, partially broken away views of the dental tray shown in FIG. 1, illustrating its operation.

Notches 68a, 68b (see FIGS. 1 and 2) are formed in inner sides of the compression members 56a, 56b, respectively, cooperating to define an opening 70 in the compression section 50. The opening 70 communicates with a cavity 72 (see FIGS. 4 and 5) formed within the compression section 50 for purposes to be discussed hereinbelow.

Now referring to FIGS. 1 and 3, the inner member 14 is assembled with the outer member 12 by inserting the handle 52 of the inner member 14 through the opening 44 in the outer member 12. More particularly, the handle 52 of the inner member 14 is placed in the track 46 formed in the handle 18 of the outer member 12, while the compression section 50 of the inner member 14 is positioned on the recessed area 36 of the outer section 12 such that it covers the ramp 40. In this manner, a generally U-shaped trough 74 is formed between the outer wall 22 of the outer member 12 and the compression section 50 of the inner member 14 for receiving a conventional impression taking material.

Figure 6:
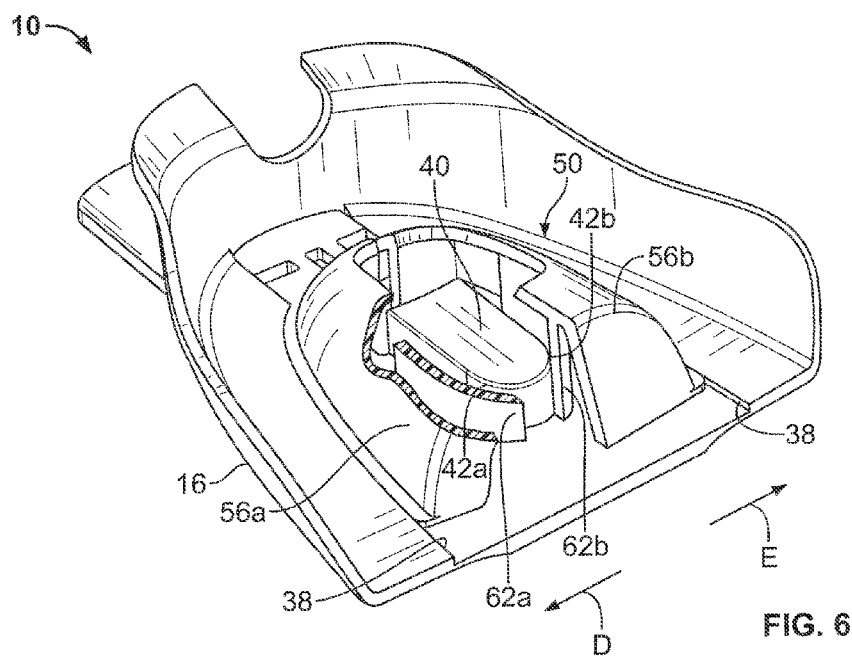

When the compression section 50 is properly assembly with the tray 16 (see FIG. 1), the compression section 50 is movable relative to the tray 16 in an axial direction generally parallel to the longitudinal axis A (as indicated by arrow B in FIG. 5) between its rest position (see FIG. 5) and its retracted position (see FIG. 6). More particularly, in the rest position of the compression section 50, the compression members 56a, 56b are in their respective retracted positions such that they are placed in an abutting fashion with respect to one another (see FIG. 5). In the retracted position of the compression section 50, the compression members 56a, 56b move to their respective expanded positions, in which they are positioned away from each other in a lateral direction (as indicated by arrow C in FIG. 5). When the compression section 50 is in its rest position, spaces 76a, 76b (see FIGS. 1 and 5) are formed between the compression member 56a and the edge 38 and between the compression member 56b and the edge 38, respectively, so as to allow the compression members 56a, 56b to move from their respective retracted positions to their respective expanded positions.

In use, an impression material (not shown) is placed in the U-shaped trough 74 formed between the tray 16 and compression section 50. The compression material can be any conventional compression material. With the handle 18 gripped by a user (e.g., a dentist), the tray 16 and the compression section 50, as assembled, are inserted into the patient's mouth. Thereafter, the tray 16 is moved upwardly toward the pallet of the patient, causing the teeth of the patient to be pressed into the impression material in the trough 74. As the teeth are pressed into the impression material, an excess amount of the impression material flow out of the trough 74. The cavity 72 is adapted to receive an overflow of the impression material through the opening 70 of the compression section 50.

Once the tray assembly 10 is properly positioned in relation to the teeth, the tab 54 of the handle 58 of the inner member 14 is pulled forward in the axial direction (as indicated by arrow B in FIG. 5) such that the compression section 50 moves axially toward the front end 26 of the tray 16 (i.e., to its retracted position). As the compression section 50 moves in the forward axial direction, the guides 62a, 62b of the compression section 50 engage the curved wall portions 42a, 42b, respectively, of the ramp 40, causing the compression members 56a, 56b to move in the lateral direction away from each other (i.e., to their respective expanded positions), as indicated by arrows D and E, respectively, in FIG. 6. As the compression members 56a, 56b expand laterally, they press against the impression material so as to ensure that the impression material is properly applied against the teeth of the patient. In this regard, the edge 38 of the tray 16 is adapted to engage the compression members 56a, 56b so as to inhibit or prevent them from expanding beyond a predetermined extent (see FIG. 6). With the compression members 56a, 56b positioned in their expanded positions, the dental tray assembly 10 is held in place until the impression material cures. Thereafter, the tray assembly 10 is removed from the patient's mouth, and the impression material is removed from the tray assembly 10.

It should be appreciated that the tray assembly 10 of the present invention provides a number of advantages over the prior art discussed above. For instance, the compression members 56a, 56b are adapted to apply additional pressure against an impression material such that the impression material is properly pressed against teeth. As a result, an accurate impression of the teeth can be taken with the use of the tray assembly 10. Moreover, because the handle 52 of the inner tray member 14 is provided in the track 46 of the outer tray member 12, the axial movement of the compression section 50 can be effected with the use of one hand (e.g., with the handle 18 gripped by a person's hand, the tab 54 can be pulled with the index finger of that hand).

It should also be noted that the tray assembly 10 of the present invention can have numerous modifications and variations. For instance, while the tray assembly 10 is adapted for use in taking an impression of upper teeth, it can be modified for use in conjunction with lower teeth. Moreover, the compression section 50 can be modified to have a different shape.

FIGS. 7-10 illustrate a teeth shade chart or guide 80 constructed in accordance with an embodiment of the present invention. More particularly, the chart 80 is adapted for use in determining the shade and/or color (collectively, "shade") of a person's tooth or teeth 82 (see FIG. 11). The chart 80 includes a substrate or carrier 84, which is made from any suitable material, such as plastic, paper, metal, etc. The substrate 84 may be flexible or substantially rigid. In one embodiment, the substrate 84 is in the form of a sheet (see FIG. 8).

Peel-off shade stickers or chips 86a-86e are removably attached to the substrate 84 of the chart 80. In one embodiment, the stickers 86a-86e have tooth shades that are common in typical people. For instance, the stickers 86a-86e are provided with shades corresponding to shade codes A1, A2, A3, A3.5 and A4, respectively, of the shade guide sold under the trademark VITA. Shade codes corresponding to the shades of the stickers 86a-86e are indicated on the substrate 84 therebelow. The chart 80 can be provided with one or more peel-off stickers having additional shades that are common in people. In one embodiment, the stickers 86a-86e are arranged linearly in a horizontal row. The stickers 86a-86e are adapted for use by an individual for determining the existing shade of the individual's tooth or teeth, as will be discussed in greater detail hereinbelow.

Peel-off shade stickers or chips 88a-88e (see FIG. 7) are also removably attached to the substrate 82 of the chart 80. In one embodiment, the stickers 88a-88e have tooth shades that are brighter or whiter than those of the stickers 86a-86e (i.e., shades that are brighter or whiter than those that are common in people). For instance, the stickers 88a-88e can be provided with shades A0, A-1, A-2, A-3 and A-4, respectively, of the shade guide sold under the trademark VITA. The chart 80 can be provided with one or more peel-off stickers having additional brighter or whiter shades. Shade codes corresponding to the shades of the stickers 88a-88e are indicated on the substrate 84 therebelow. In one embodiment, the stickers 88a-88e are arranged linearly on the substrate in a horizontal row below e stickers 86a-86e. The stickers 88a-88e are adapted for use by an individual for selecting the tooth shade that he/she wishes to achieve by way of a tooth whitening tool or procedure and/or for determining whether he/she has achieved a selected tooth shade.

Figure 9:
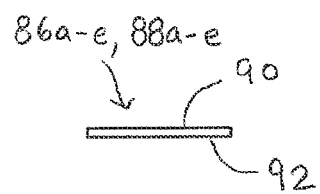
FIG. 9 is a side view of one of a plurality of shade stickers provided on the shade chart of FIG. 7.

Referring to FIG. 9, each of the stickers 86a-86e, 88a-88e includes a front surface 90 and a rear surface 92. The front and rear surfaces 90, 92 of each of the stickers 86a-86e, 88a-88e are substantially smooth (i.e., planar). In one embodiment, the rear surface 92 of each of the stickers 86a-86e, 88a-88e is not applied with any adhesive material. In such circumstances, the substrate 84 is provided with a layer of adhesive material such that the stickers 86a-86e, 88a-88e can be removably attached thereto. In another embodiment, the rear surface 92 of each of the stickers 86a-86e, 88a-88e includes a layer of adhesive material for removably attaching the stickers 86a-86e, 88a-88e on the substrate 84. Laminates or films 94, 96 (see FIGS. 7 and 8) can be optionally provided on the substrate 84 so that the stickers 86a-86e, 88a-88e, respectively, can be removably attached thereto so as to facilitate their removal from the substrate 84.

Referring to FIG. 9, each of the stickers 86a-86e, 88a-88e is provided with a substantially planar or sheet-like construction. In one embodiment, each of the stickers 86a-86e, 88a-88e is provided with a thickness in the range of from about 0.005 mm to about 0.5 mm. In another embodiment, the thickness of each of the stickers 86a-86e, 88a-88e ranges from about 0.1 mm to about 0.3 mm.

In one embodiment, each of the stickers 86a-86e, 88a-88e is provided with a translucency that is similar to the translucency of the enamel layer of a typical person's tooth. For instance, the translucency of each of the stickers 86a-86e, 88a-88e may be within the range of from about 50% to about 95%. Alternatively, the translucency of each of the stickers 86a-86e, 88a-88c may range from about 65% to about 85%.

Figure 10:
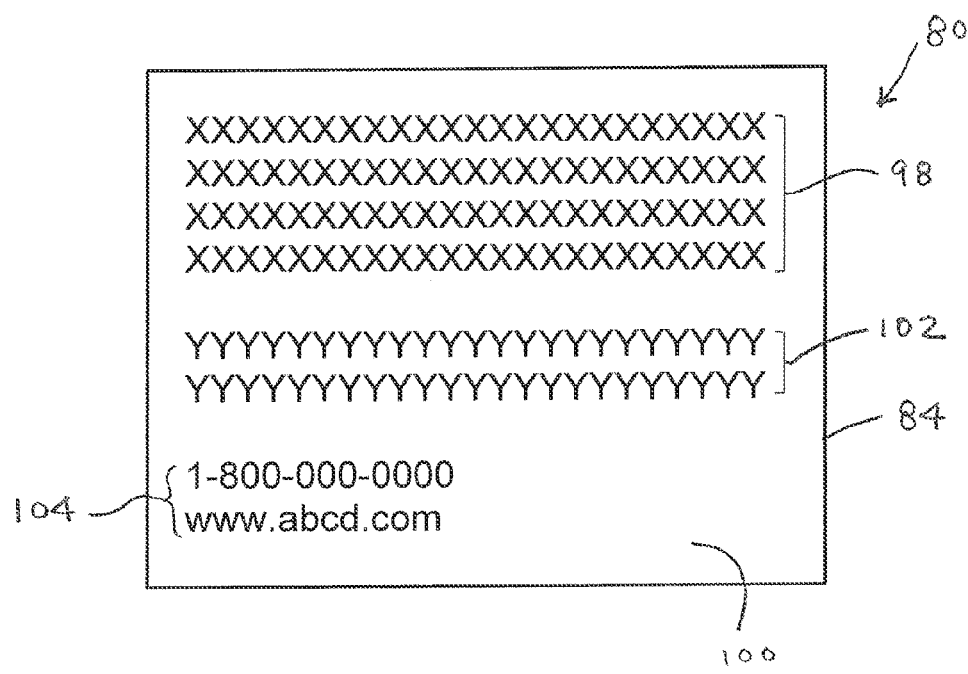
FIG. 10 is a view of a reverse side of the shade chart of FIG. 7.

With reference to FIG. 10, instructions 98 for using the chart 80 are provided on a reverse side 100 of the chart 80 opposite the side to which the stickers 86a-86e, 88a-88e are attached. Additional instructions 102 and information 104 are provided on the side 100 of the chart 80 for purposes to be discussed below.

In use, one of the stickers 86a-86e is selectively removed from the substrate 84 by a user. The removed sticker (e.g., the sticker 86c) is then applied directly to a selected one of the user's teeth 82 (e.g., one of the two maxillary central incisors) such that the sticker 86c temporally sticks and lays flat against the surface of the selected tooth 82 (see FIG. 11). As discussed above, the rear surface 92 of the sticker 86c may be provided with an adhesive material so as to facilitate the adhesion of the sticker 86c to the tooth 82. Alternatively, the rear surface 92 of the removed sticker 86c and/or the surface of the selected tooth 82 may be applied with the user's saliva or other liquid substances (e.g., the user licks the rear surface 92 of the removed sticker 86c and/or the surface of the selected tooth 82 with his or her tongue) such that the sticker 86c can be removably and temporarily attached to the selected tooth 84 by the adhesive property of the saliva.

Figure 11:
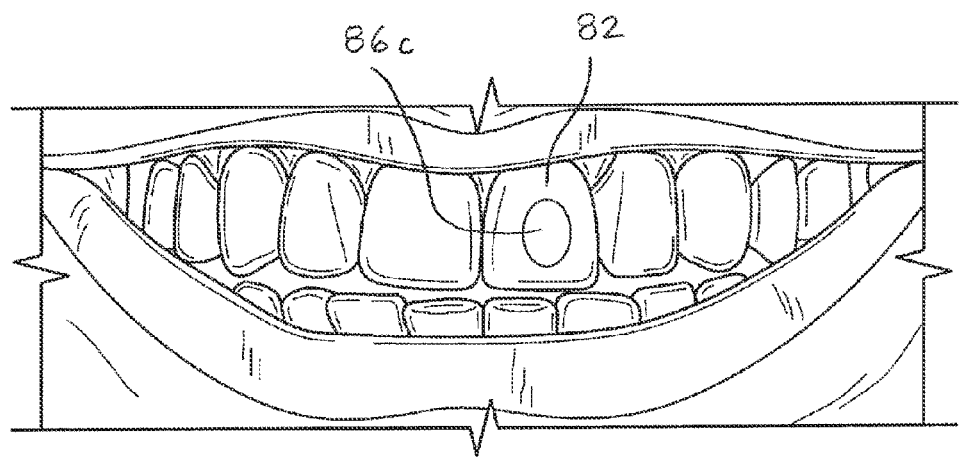
FIG. 11 is a schematic view of a person's teeth and one of the shade stickers shown in FIGS. 1-9.

As illustrated in FIG. 11, the sticker 86c is applied to the tooth 82 such that the sticker 86c is positioned substantially at the center of the tooth 82. That is, the sticker 86c is superimposed directly on the tooth 82 such that all sides of the sticker 86a are surrounded by the surface of the tooth 82. As a result, the shade of the tooth 82 can be compared easily to the shade of the sticker 86c. Moreover, the adhesive material on the sticker 86c and/or the saliva applied thereto create a continuous connection or contact substantially throughout the interface between the tooth 82 and the sticker 86c. This connection or contact functions to blend the translucency of the sticker 86c with the translucency of the enamel layer of the tooth 82. The blended translucency of the sticker 86c and the tooth 82 mimics the translucency of an actual tooth enamel layer so as to allow a realistic and accurate shade matching between the sticker 86c and the tooth 82.

If the shade of the sticker 86c does not match with the shade of the tooth 82, the sticker 86c is removed and placed on a suitable place (e.g., back on the substrate 84). Another sticker (i.e., one of the stickers 86a, 86b, 86d and 86e remaining on the substrate 84) is removed from the substrate 84 and applied to the tooth 82 in the manner discussed above. For instance, if the shade of the initially selected sticker 86c is lighter than the shade of the tooth 82, then a darker-shaded sticker (e.g., one of the stickers 86d, 86e) is selected and applied to the tooth 82. This process is repeated until the user locates a matching one of the stickers 86a-86e, thereby allowing the user to determine the shade of his/her teeth.

Figure 12:
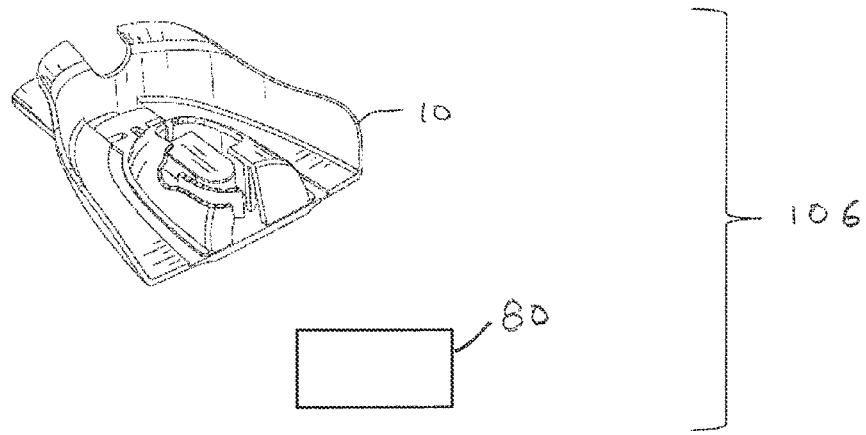
FIG. 12 is a view of a kit constructed in accordance with an embodiment of the present invention.

With reference to FIG. 12, a kit 106 is provided in accordance with an embodiment of the present invention. More particularly, the kit 106 includes the chart 80 and the dental tray assembly 10 of the embodiment shown in FIGS. 1-6. The kit 106 can be provided directly to an end user, rather than a dental professional (e.g., a dentist), such that it can be used by the user in ordering one or more custom-made dental products directly from a dental laboratory without visiting or otherwise involving any dentist. The dental products include, without limitation, flippers (e.g., custom tooth inserts), sports mouthguards, dental night guards, custom whitening trays, novelty costume teeth (e.g., "Dracula" teeth, etc.), custom trays for providing a temporary preview of a person's teeth as disclosed in U.S. patent application Ser. No. 13/285,315 filed Oct. 31, 2011 (published as U.S. Patent Publication No. 2013/0108989 A1), orthodontic trays (e.g., those sold under the trademark INVISALIGN), orthodontic retainers, etc. The dental tray assembly 10 may be replaced with any conventional dental tray for taking an impression of the user's teeth.

In use, once the user determines the shade of his/her teeth using the chart 80 as discussed above, the dental tray assembly 10 is used by the user to take a dental impression of his/her teeth in the manner described above in conjunction with the embodiment of FIGS. 1-6. After the dental impression has been taken, it is sent to a dental laboratory via mail or another delivery method (e.g., via messenger) together with the shade information or code of the matching sticker (i.e., one of the stickers 86a-86e) and the identification of the dental product or products that he/she wishes to order. Using the dental impression and the shade code provided by the user, the ordered dental products are custom-made by the dental laboratory for the user. Once the dental products are completed, they are sent to the user via mail or another delivery method.

Figure 13:
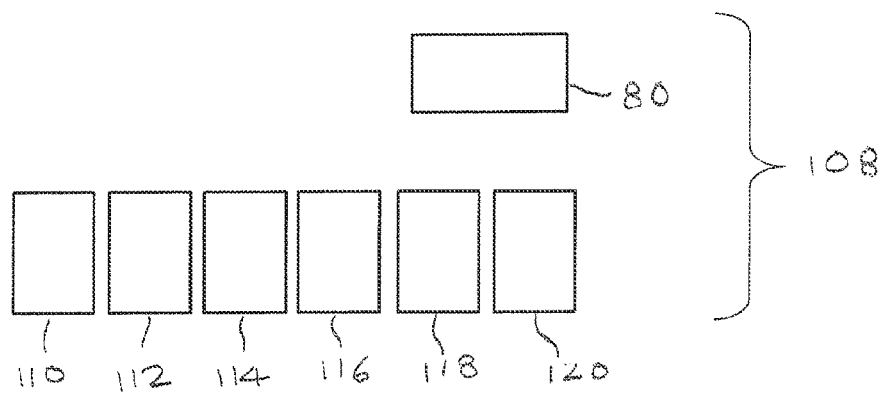
FIG. 13 is a view of a kit constructed in accordance with an embodiment of the present invention.

Referring to FIG. 13, one embodiment of the present invention involves providing a dental whitening kit 108 including the chart 80. The kit 108, which may be provided directly to an end user, includes one or more conventional whitening kit components, such as a whitening strips 110, whitening gel 112, a mouth tray 114 for receiving the whitening gel therein for application to a person's teeth, an applicator 116 for applying the whitening gel (optionally preloaded with the whitening gel 112), an after-whitening remineralization gel 118 to reduce tooth sensitivity, and/or an applicator 120 for applying the remineralization gel, etc., all of which are illustrated schematically in FIG. 13.

The whitening components of the kit 108 are used in a conventional manner to whitening a user's teeth. Prior to the initiation of a whitening process, the user determines the original shade of his/her teeth (hereinafter "original tooth shade") by matching same with one of the stickers 86a-86e. In this regard, the chart 80 may be provided with a space on which the user can record the code corresponding to the original tooth shade. After the completion of the whitening process, the user determines which of the stickers 86a-86e matches with the shade of his/her whitened teeth (referred to hereinafter as "the whitened shade"). If the user's teeth have been whitened beyond the shades of the stickers 86a-86e, the user may use the stickers 88a-88e, which have lighter or whiter shades than those of the stickers 86a-86e. The stickers 88a-88e are used in a method identical to the method discussed above in conjunction with the stickers 86a-86e. By comparing the sticker 86a-86e, 88a-88e matching with the whitened shade to the sticker corresponding to the original tooth shade, the user can determine the effectiveness of the whitening process (e.g., the degree by which his/her teeth have been whitened).

In accordance with one embodiment, the kit 108 may also include the dental tray assembly 10 of the embodiment illustrated in FIGS. 1-6. By including the dental tray assembly 10 in the kit 108, the user may take an impression of his or her dental tray prior to the initiation of the whitening process and send the dental impression to a dental laboratory such that a custom-fit mouth tray may be made for him/her for the application of the whitening gel to his/her teeth. In such circumstances, the mouth tray 114 illustrated in FIG. 13 may be omitted from the kit 108.

Figure 14:
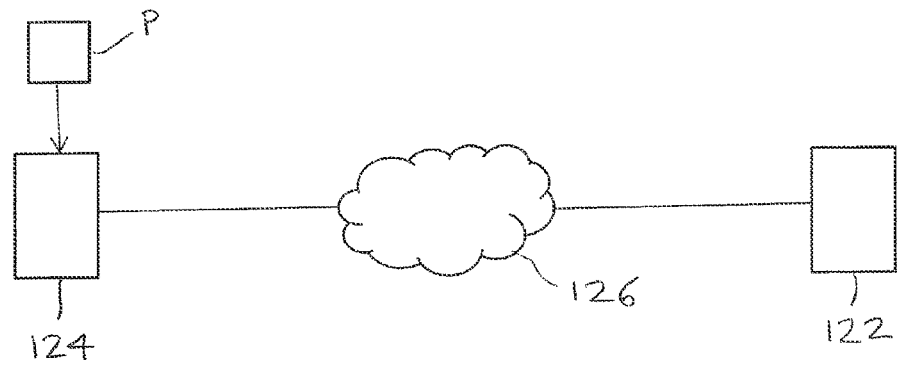
FIG. 14 is a schematic view of a system constructed in accordance with an embodiment of the present invention for determining the shade of a person's teeth.

In accordance with one embodiment of the present invention, another method is provided for determining the shade of a person's teeth. One of the stickers 86a-86e (e.g., the sticker 86b) is removed from the chart 80 and is applied to one of the person's teeth, as described above. An analog or digital photograph P (see FIG. 14) of the person's teeth and the sticker 86b attached thereto is taken with a camera. The photograph P is then used for determining the shade of the teeth by using the shade of the sticker 86b as a reference shade. In one embodiment, the photograph P is transmitted to a computerized processor 122 (e.g., a remotely located central server equipped with a microprocessor) together with the shade code of the selected sticker 86b. The photograph P and the shade code can be sent to the processor 122 in any conventional manner, such as via data uploading website, email, text message, etc. For instance, when the photograph P is taken with the use of a digital camera included in a portable communication device 124 (see FIG. 14), such as a smart phone, the photograph P and the shade code of the sticker 86b can be sent directly from the portable communication device to the processor 122 via a conventional network 126 (e.g., the Internet or a mobile communication network). Alternatively, the communication device 124 can be a separate component from the digital camera, being adapted to receive the photograph P for transmission to the processor 122. The instructions 102 and information 104 are included on the side 100 of the chart 80 for providing instructions and information for the transmission of the photograph P and the shade code website address for directly uploading materials to the processor 122, an email addresses for sending materials to the processor 122, etc.).

Once the processor 122 receives the photograph P and the shade code of the sticker 86b, it uses the shade of the sticker 86b as a reference shade to determine the shade of the teeth. More particularly, the processor 122 compares the shade of the teeth in the photograph P to the shade of the sticker 86b. Since the processor 122 is provided with the shade code of the to sticker 86b (i.e., shade code A2), it is able to determine the shade code corresponding to the teeth. The shade code of the teeth as determined by the processor 122 is then transmitted to the user (e.g., to the communication device 124) in a conventional manner.

As discussed above, the processor 122 is adapted to determine the shade of the teeth by comparing the shade of the teeth in the photograph P to the shade of the sticker 86b, the shade code of which is provided to the processor 122. In such circumstances, the chart 80 may contain a single shade sticker for use in conjunction with this process.

In one embodiment, a computer application or program for determining the shade of the teeth from the photograph P can be stored locally on the communication device. In this manner, the photograph P and the shade code of the sticker 86b need not be transmitted to the processor 122.

Figure 7:
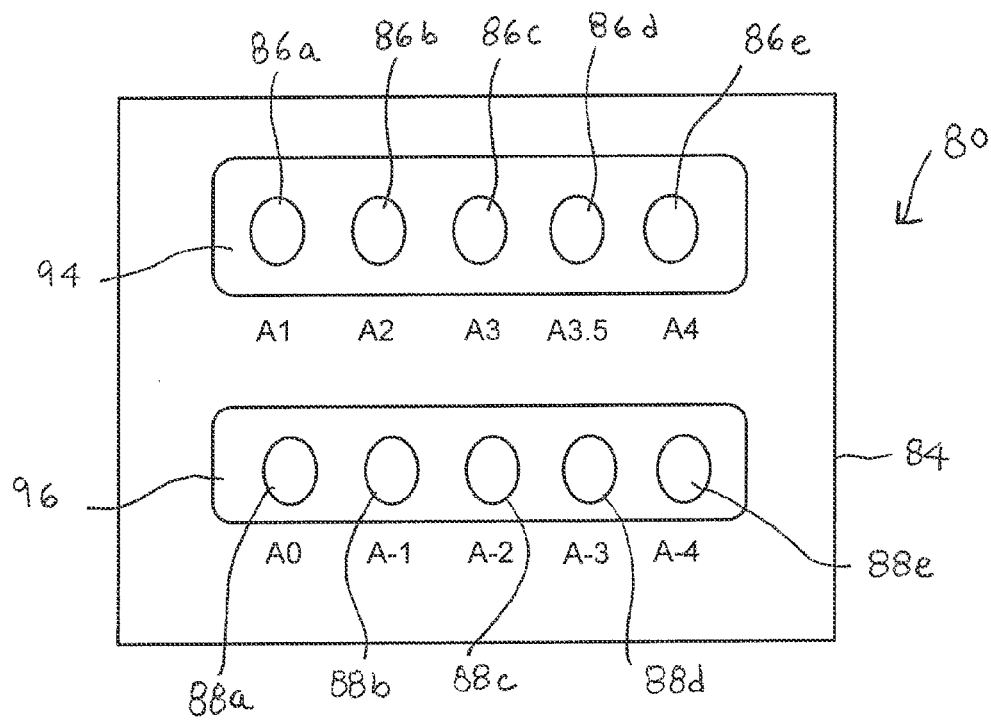
FIG. 7 is a top plan view of a shade chart constructed in accordance with an embodiment of the present invention.
Figure 8:
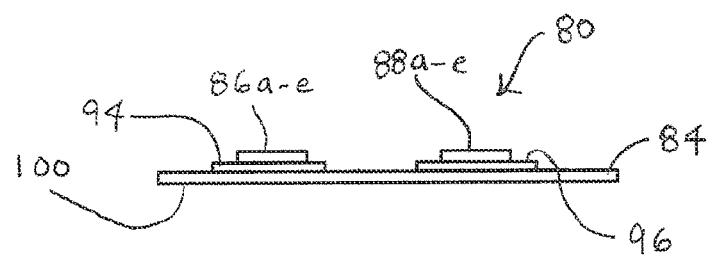
FIG. 8 is a side view of the shade chart shown in FIG. 7.
Figure 15:
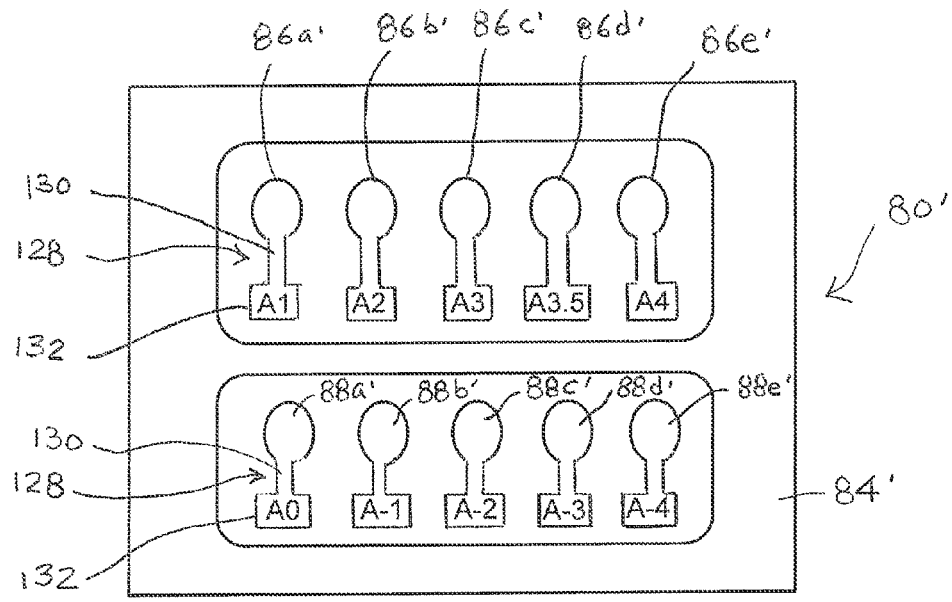
FIG. 15 is a view of a modified version of the shade chart shown in FIG. 7.
Figure 16:
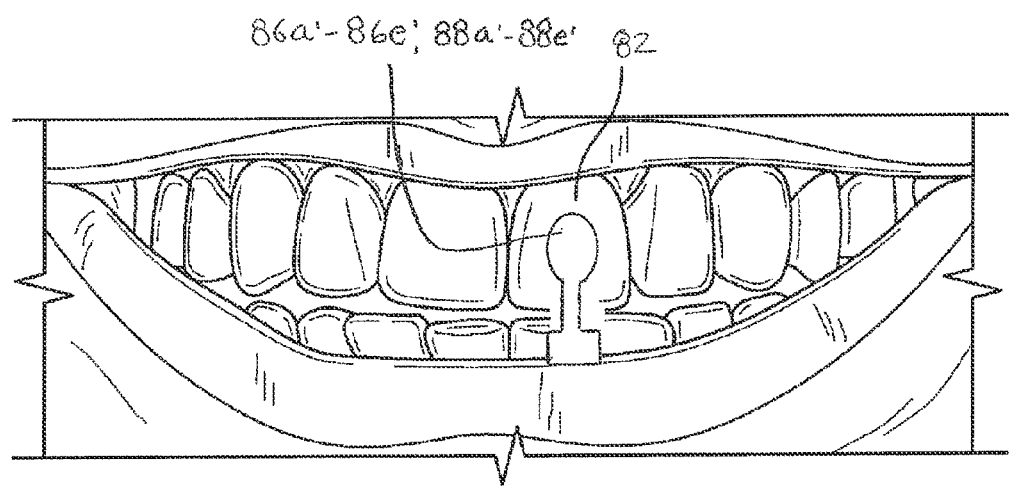
FIG. 16 is a schematic view of a person's teeth and one of a plurality of shade stickers of the shade chart shown in FIG. 15.

FIG. 15 illustrates a shade chart 80', which is a modified version of the shade chart 80 illustrated in FIG. 7. The shade chart 80' of FIG. 15 is constructed, assembled and used in the same basic manner as the shade chart 80 of FIG. 7, except as discussed below. The shade chart 80' includes a plurality of shade stickers 86a'-86e' and a plurality of shade stickers 88a'-88e'. Each of the stickers 86a'-86e', 88a'-88e' includes a handle 128 so as to facilitate the handling of a corresponding one of the stickers 86a'-86e', 88a'-88e' by a user. The handle 128 of each stickier 86a'-86e', 88a'-88e' includes a stem 130 connected (integrally or otherwise) to a corresponding one of the stickers 86a'-86e', 88a'-88e' and a base 132 connected thereto. The base of each sticker 86a'-86e', 88a'-88e' has a sufficient size such that it can be gripped by a user for handling purposes and/or such that a corresponding shade code can be indicated thereon. The handles 128 can be attached to a substrate 84' of the chart 80' in the same manner as the stickers 86a-86e and the stickers 88a-88e of the chart 80 shown in FIG. 7. Alternatively, the handles 128 may be loose from (i.e., not attached to) the substrate 84' so as to facilitate the removal of their corresponding stickers 86a'-86e' and the stickers 88a'-88e' from the substrate 84'. FIG. 16 illustrates one of the stickers 86a'-86e', 88a'-88e' removably applied to one of a person's teeth 82.

It will be understood that the embodiments described herein are merely exemplary and that a person skilled in the art may make many variations and modifications without departing from the spirit and scope of the invention. All such variations and modifications, including those discussed above, are intended to be included within the scope of the invention as defined in the appended claims.

I claim:

1. A kit comprising:
   a device for use in determining the shade of a person's tooth having a front surface, said device including at least one shade sticker having a predetermined shade, said at least one sticker having a size smaller than the tooth and configured so as to be removably attached to the front surface of the tooth such that said at least one sticker can be superimposed directly on the front surface of the tooth; and a dental tray for use in taking an impression of a person's teeth, said dental tray including a first section, which has a longitudinal axis and a generally U-shaped outer wall, and a second section, which has a dome-shaped inner member sized and shaped so as to be mounted at least partially within said U-shaped wall of said first section, said U-shaped wall and said dome-shaped member being sized and shaped so as to define a trough therebetween for receiving an impression-taking material, said second section being movable relative to said first section in a first direction which is substantially parallel to said longitudinal axis of said first section, said dome-shaped member having first and second movable members movably attached to said second section, each of said first and second movable members being movable in a second direction substantially perpendicular to said longitudinal axis in response to the movement of said second section in said first direction.

2. The kit of claim 1, further comprising one of a whitening gel or whitening strips.

3. The kit of claim 1, wherein the device includes a substrate, said at least one sticker being removably attached to said substrate.

4. The kit of claim 3, wherein said at least one sticker is adapted to be peeled off said substrate.

5. The kit of claim 3, wherein said at least one sticker has a substantially planar construction.

6. The kit of claim 5, wherein said at least one sticker has a thickness within a range of from about 0.005 mm to about 0.5 mm.

7. The kit of claim 1, wherein said at least one sticker has a translucency that is comparable to a translucency of an enamel layer of a conventional tooth.

8. The kit of claim 7, wherein said translucency of said at least one sticker is within a range of from about 50% to about 95%.

9. The kit of claim 1, wherein said at least one sticker includes a plurality of stickers, each of which is sized and shaped so as to be removably attached to the front surface of the tooth such that each of said plurality of stickers can be superimposed directly on the front surface of the tooth.

10. The kit of claim 1, wherein said at least one sticker includes a handle so as to facilitate the handling of said at least one sticker.

* * * * *